United States Patent
Sharma et al.

(10) Patent No.: US 11,844,821 B2
(45) Date of Patent: Dec. 19, 2023

(54) FENUGREEK EXTRACT FOR THE TREATMENT OF POLY CYSTIC OVARIAN SYNDROME (PCOS)

(71) Applicant: Pawan Kumar Goel, Panchkula (IN)

(72) Inventors: Ashok Sharma, Panchkula (IN); Kiran Tewari, Panchkula (IN)

(73) Assignee: Pawan Kumar Goel, Panchkula (IN)

( * ) Notice: Subject to any disclaimer, the term of this patent is extended or adjusted under 35 U.S.C. 154(b) by 265 days.

(21) Appl. No.: 17/007,180

(22) Filed: Aug. 31, 2020

(65) Prior Publication Data

US 2021/0093686 A1 Apr. 1, 2021

Related U.S. Application Data

(63) Continuation of application No. 15/524,757, filed as application No. PCT/IN2015/000079 on Feb. 11, 2015, now abandoned.

(30) Foreign Application Priority Data

Dec. 16, 2014 (IN) .......................... 3718/DEL/2014

(51) Int. Cl.
*A61K 36/48* (2006.01)
*A61K 9/00* (2006.01)
*A61K 9/48* (2006.01)
*A61K 31/7048* (2006.01)

(52) U.S. Cl.
CPC ............ *A61K 36/48* (2013.01); *A61K 9/0053* (2013.01); *A61K 9/48* (2013.01); *A61K 31/7048* (2013.01)

(58) Field of Classification Search
CPC ........ A61K 36/48; A61K 9/0053; A61K 9/48; A61K 31/7048; A61P 15/00; A61P 15/08; A61P 43/00
See application file for complete search history.

(56) References Cited

U.S. PATENT DOCUMENTS 8,217,165 B2 * 7/2012 Goel .................... C07J 71/0031
536/128
8,754,205 B2 * 6/2014 Goel .................... C07J 71/0031
536/128

FOREIGN PATENT DOCUMENTS

CN 104083749 A * 10/2014
IN 2007CH01766 A * 2/2012

OTHER PUBLICATIONS

Bashtian et al. "Evaluation of Fenugreek (*Trigonella foenum-graceum* L.), Effects Seeds Extract on Insulin Resistance in Women with Polycystic Ovarian Syndrome". Iranian Journal of Pharmaceutical Research, (SPR 2013) vol. 12, No. 2, pp. 475-481. (Year: 2013).*

* cited by examiner

*Primary Examiner* — Aaron J Kosar
(74) *Attorney, Agent, or Firm* — Ladas & Parry LLP

(57) ABSTRACT

Discloses is a single herb extract for the treatment of PCOS (Poly Cystic Ovarian Syndrome) when given in oral dosage form as capsules of 500 mg, twice a day for period of time ranging from 30-90 days. The extract is obtained from fenugreek seeds using a specific method of extraction and comprises five furostanolicsaponins present in synergistic ratios as in Table 1 and having analytical profile as in FIG. 1.

6 Claims, 1 Drawing Sheet

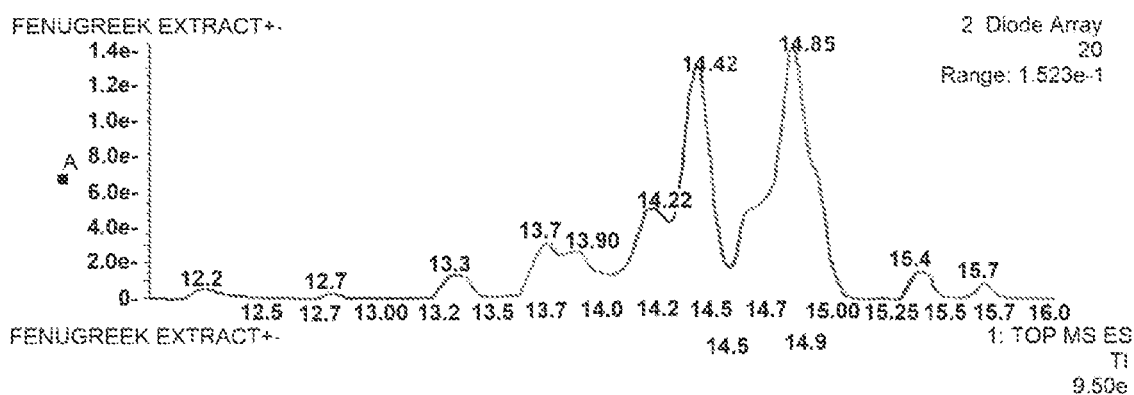

FENUGREEK EXTRACT FOR THE TREATMENT OF POLY CYSTIC OVARIAN SYNDROME (PCOS)

RELATED APPLICATION

This application is a continuation of application Ser. No. 15/524,757 filed May 5, 2017 which is a 371 of International Patent Application No.: PCT/IN2015/000079 filed on Feb. 11, 2015, which claims priority from Indian Application No.: 3718/DEL/2014 filed Dec. 16, 2014, the disclosures of which are incorporated in their entirety by reference herein.

FIELD OF INVENTION

Invention pertains to a single herb extract for the effective treatment of PCOS (Poly Cystic Ovarian Syndrome) when given in oral dosage form as capsules of 500 mg, twice a day for period of time ranging from 30-90 days. The extract is obtained from the seeds of a single herb viz. fenugreek, using a specific method of extraction.

Page 5, paragraph 1 (lines 1 and 2): furostanolic saponins from fenugreek seeds, is used which when given orally is effective in the treatment of PCOS. Calophyllum species herbs are not used at all in the present invention.

BACKGROUND OF INVENTION

About PCOS: Polycystic ovary syndrome (PCOS) is one of the most common endocrine disorders among females. PCOS has a diverse range of causes that are not entirely understood, but there is evidence that it is largely a genetic disease. Polycystic ovary syndrome (PCOS) is a problem in which a woman's hormones are out of balance. It is commonly associated with failure of ovulation Polycystic Ovary Syndrome (PCOS) is an endocrine disorder which affects 10-15% of the female population. This syndrome represents the most common hormonal disorder in women of reproductive age.

The symptoms and severity of the disease vary greatly among women. In women with PCOS, the physiological hyperinsulinaemia of adolescence may constitute a triggering factor that brings about the development of hyper androgenism and anovulation.

Causes: Polycystic ovary syndrome has a basic etiology linked to an oxidative syndrome with insulin resistance. The insulin resistance and consequent hyperinsulinaemia that are often associated with this syndrome play an important role not only in the pathogenesis of the syndrome itself, but also in the clinical symptomatology. The chronic anovulation typical of PCOS results in an increased number of atretic follicles (which become cysts) and increased interstitial tissue in the stroma of the ovaries.

Mechanisms involved in PCOS: Under normal conditions, women produce a single dominant follicle that participates in a single ovulation each menstrual cycle. The process begins when a cohort of primordial follicles is recruited to initiate growth. Successive recruitment gives rise to the primary, secondary, tertiary and graafian follicles present in the ovaries. The ability to become a dominant follicle is not a characteristic shared by all follicles, and those that lack the property die by atresia due to increased androgens. In the human female, only about 400 of the original 7 million follicles survive atresia and give rise to dominant follicles.

In patients with PCOS, the process of folliculogenesis does not proceed normally. The initial steps, recruitment and growth to the small graafian stages, are functioning in PCOS, but the terminal step, the selection of dominant follicles that can ovulate, does not occur regularly. Viable follicles seldom develop beyond about the 6 mm stage. In some unexplained way, this condition leads to the accumulation of large numbers of small graafian follicles (commonly referred to as cysts) in which the theca interstitial cells (TIC) produce abnormally large amounts of androgen, but the granulosa cells (GC) fail to express the aromatase enzyme and aromatize the androgen substrate to estradiol. Consequently, a state of continued hyperandrogenism results. The problem is self-perpetuating in part because the atretic follicle becomes an androgenic follicle by a "default" mechanism: because of low aromatase activity in atretic follicles, androstenedione is preferentially metabolized to testosterone and hence to dihydrotestosterone within the ovary (Poison et al (1988): *Polycystic ovaries—a common finding in normal women, The Lancet Volume* 331, Issue 8590, 16 Apr. 1988, Pages 870-872DOI: 10.1016/S0140-6736(88)91612-1).

Diagnosis of PCOS

Gynecologic ultrasonography—specifically looking for small ovarian follicles help to detect PCOS. Small ovarian follicles are believed to be the result of disturbed ovarian function with failed ovulation, reflected by the infrequent or absent menstruation that is typical of the condition. In PCOS, there is a so-called "follicular arrest"; i.e., several follicles develop to a size of 5-7 mm, but not further. No single follicle reaches the preovulatory size (16 mm or more).

Laparoscopic examination—it may reveal a thickened, smooth, pearl-white outer surface of the ovary.

Increase in hormonal level—Serum (blood) levels of androgens (male hormones), including androstenedione and testosterone may be elevated. The free testosterone level is thought to be the best measure with 60% of PCOS patients demonstrating supranormal levels. The ratio of LH (Luteinizing hormone) to FSH (Follicle-stimulating hormone), when measured in international units, is elevated in women with PCOS Anti-Müllerian hormone (AMH) is increased in PCOS, and may become part of its diagnostic criteria.

Treatment: Pharmaceutical medications which are prescribed for PCOS include:
i. Combination estrogen and progestin hormones: birth control pills, vaginal rings, or skin patches. These hormones correct irregular menstrual bleeding or absent menstrual cycles.
ii. Synthetic progestin: It makes endometrial lining build up and shed. This shedding prevents uterine cancer.
iii. Androgen-lowering spironolactone (Aldactone): Diuretic. It is often used with estrogen-progestin therapy.
iv. Metformin (Glucophage):This diabetes medicine is a newer PCOS treatment for controlling insulin, blood sugar levels, and androgen levels.
v. Clomiphene (Clomid, Serophene) (fertility medicines) and gonadotropin injections (LH and FSH).
vi. Medroprogesterone acetate
vii. Gonadotrophin releasing hormone agonists
viii. Glucocorticoids
ix. Ketoconszole, flutamide, finasteride and metformin. (Source:http://www.webmdcom)

However, none of the treatments is specific for the effective treatment of PCOS as they include the combinations of hormones to treat PCOS which have side effects also. So there is a need to develop safer formulations e.g. from herbal extracts to treat polycystic ovary syndrome.

Herbal Extracts for the Treatment of PCOS

PRIOR ART

US Patent Application No. 20070298049 (2003) discloses a therapeutic agent for treating polycystic ovary syndrome (PCOS). The agent comprises an extract of mushrooms as an active ingredient which exhibits few, if any, side effects. It is effective at inducing ovulation and is safely available for not only females who desire to bear children, but also for unmarried or young females. The present invention is different from this prior art because it discloses an extract of furostanolicsaponins from fenugreek seeds to be given orally for the effective treatment of PCOS and does not contain any mushrooms or its extract at all.

U.S. Pat. No. 8,062,680 (2005) discloses a method for treating Polycystic Ovary Syndrome in a patient wherein the method comprising administering to the patient, together with pharmaceutically acceptable excipients, a composition comprising effective amounts of: natural herbs vizRhodiolarosea root extract, Panaxquinquefolius root extract, Pfaffiapaniculada, etc. In contrast in the present invention, no such herbs are used at all. It is not a mixture of herbs but extract obtained from seeds of a single herb i.e. fenugreek.

WO Patent Application No. 2008119131 (2007) discloses a composition for PCOS treatment comprising several herbs viz. Shu Di Radix rehmanniae, Shan Yao Radix disocorea, Shan Yu Rou Fructuscorniofficinalis etc. In contrast in the present invention, no such herbs are used at all. It is not a mixture of these herbs but a well-defined extract obtained from seeds of a single herb i.e. fenugreek.

CN Patent Application No. 102847081 (2011) discloses a complex mixture of herbs for PCOS treatment. However, the present invention is not a complex mixture of the herbs but a well-defined extract obtained from seeds of a single herb i.e. fenugreek. Fenugreek is not disclosed at all in the prior art patent.

WO Patent Application No 2013136257 (2012) discloses an herbal composition comprising a therapeutically effective amount of the extract of a plant belonging to Calophyllum species as an active ingredient and optionally, a pharmaceutically acceptable carrier. The composition is formulated for oral administration in the form of a tablet, capsule or granules used in the treatment of a metabolic disorder like insulin resistance, hyperglycemia, type 2 diabetes, polycystic ovary syndrome or related. However in the present invention an extract of furostanolic saponins from fenugreek seeds, is used which when given orally is effective in the treatment of PCOS. Calophyllum species herbs are not used at all in the present invention.

Articles

Wang et al (2007) have disclosed the use of cinnamon to treat PCOS. The patients were exposed to cinnamon extracts orally and they showed positive results (The effect of cinnamon extract on insulin resistance parameters in polycystic ovary syndrome: a pilot study Fertility and Sterility Volume 88, Issue 1, July 2007, Pages 240-243). In contrast, the present invention discloses use of furostanolic saponins extracts from fenugreek seeds. which when given orally are effective in the treatment of PCOS. Cinnamon extracts are not used in the present invention at all.

Ethan Basch et al (2003) has reviewed the therapeutic applications of fenugreek. (*Therapeutic Applications of Fenugreek, Alternative Medicine Review Volume* 8, *Number* 1, 2003, Pages 20-27). Fenugreek and its extracts have been found to have good therapeutic applications in the treatment of Diabetes and also lowering lipid levels. The review does not disclose use of fenugreek extracts for the treatment of PCOS specifically. Moreover, the extract of fenugreek seeds as disclosed in the present invention is a specific, analytically defined extract.

Kassem A. et al (2006) evaluated antifertility effect of whole fenugreek seeds. In their study they exposed the rabbits to feeding diets containing 30% fenugreek seeds. The seeds had significant effect on the pre breeding estrogen concentrations in the treated animals. (*Evaluation of the potential antifertility effect of fenugreek seeds in male and female rabbits, Contraception Volume* 73, Issue 3, March 2006, Pages 301-306, DOI. 10.1016/j.contraception.2005.08.020). However, Kassem et al does not disclose any formulation or fenugreek extract for the treatment of PCOS specifically.

Bashtian M. H. et al (2013) discloses effects of fenugreek seed extracts as adjuvant therapy with metformin, for the treatment of woman with PCOS. It was a prospective randomized, double-blind, placebo-controlled trial. Women were randomly allocated to receive hydroalcoholic extract of fenugreek seeds in capsules (500 mg dosage form) along with metformin (500 mg dosage form) and were assessed for improvement. The results showed significant decrease in PAO (polycystic appearing ovaries) in group. (*Evaluation of Fenugreek* (*Trigonellafoenum-graceum* L.), *Effects Seeds Extract on Insulin Resistance in Women with Polycystic Ovarian Syndrome, Iran J Pharm Res.* 2013 *Spring,* 12(2): 475-481).

The extract used in the study and its method of preparation has been disclosed by Bashtian as below:

Dried and fresh fenugreek seeds (25 Kg) were obtained from a commercial source. Seeds were washed in distilled water and were ground to a fine powder in a mixer under chilled conditions. Obtained powder was extracted by percolated white ethanol (70% w/w). The ethanol extract was lyophilized. The lyophilized extract was 2600 g. Twenty-five percent of tricalcium phosphate was added to dried extract. The powder mixture was crushed in a blinder and passed through a 20-mesh sieve. A capsule-filling machine was used for preparation of powder containing capsules. The mean weight of each capsule was 525 mg (500 mg dried extract). Placebo capsules were filled (525 mg) with lactose powder colored with 1% tartrazin.

In contrast, the present invention is not a simple, hydroalcoholic extract obtained from fenugreek seeds but a purified extract of five furostanolic saponins present in synergistic ratios and obtained from fenugreek seeds by a proprietary process developed by the inventor and for which the inventor has applied for grant of patent in India vide patent application number 1439/DEl/2008 Dated 2017 Jun. 8 entitled "A NOVEL PROCESS FOR EXTRACTION OF FUROSTANOLIC SAPONINS FROM FENUGREEK SEEDS" followed by international patent application number—PCT/IN2008/000559, subsequently filed and granted U.S. Pat. No. 8,217,165 B2 and divisional patent number U.S. Pat. No. 8,754,205 B2, filed in EUROPE as application number EP 08 808 174.0.

Analytical fingerprint of the extract is given in FIG. 1. The composition of the extract is given below in Table 1.

TABLE 1

Composition of extract (LCMS fingerprint given in FIG. 1)

| Peak No. | Elution Time (Minutes) | Compound Name | % |
|---|---|---|---|
| 1. | 13.75 | — | 7.13 |
| 2. | 13.90 | — | 4.61 |
| 3. | 14.22 | Trigoneoside IV a | 15.10 |
| 4. | 14.42 | Glycoside F | 29.36 |
| 5. | 14.85 | Protodioscin | 43.80 |

Bashtian M. H. et al. does not anticipate the extract of present invention, which is a specifically defined synergistic extract of five furostanolic saponins from fenugreek seeds, as per Table 1 above. The significant differences between extract disclosed by Bashtian et al.

| S. No. | Bashtian M. H. et al (2013) | Present invention |
|---|---|---|
| 1. | Discloses use of a hydroalcoholic extract from fenugreek seeds. | Discloses use of an analytically defined furostanolic saponin extract purified from fenugreek seeds by a proprietary process developed by the inventor for which inventor has been granted patent. |
| 2. | The extract is used for PCOS treatment as adjuvant therapy along with metformin. | The extract is not used as adjuvant therapy and therapeutic effect is obtained without use of any metformin |
| 3. | The ingredients of the extract are not known at all. | Ingredients are a well-defined mixture of five furostanolic saponins extract present in synergistic ratios (FIG. 1 and Table 1) |
| 4. | Quality of the extract cannot be controlled in absence of marker compounds. | Quality of the extract is controlled owing to use of marker compounds and development of analytical fingerprint (FIG. 1, Table 1) |

Thus, none of the prior art anticipates use of the specific extract of present invention which is obtained from the seeds of a single herb viz. fenugreek and is comprising five furostanolic saponins present in synergistic ratios and extracted from fenugreek seeds by a proprietary process developed by the inventor. The analytical profile (LCMS fingerprint) of the extract is given in FIG. 1. The extract when given orally is effective in the treatment of PCOS, at a dose of two capsules of 500 mg each for a period of time varying between 30-90 days, depending upon individual response and clinical assessment.

OBJECTS OF THE PRESENT INVENTION

It is an object of the present invention to disclose a herbal extract obtained from a single herb viz. fenugreek which is effective in the treatment of PCOS when taken orally.

Another object of the present invention is to disclose a herbal extract for the treatment of PCOS comprising five furostanolic saponins present in synergistic ratios and obtained from fenugreek seeds.

Yet another object of the invention is to disclose an oral composition obtained from extract of fenugreek seeds which leads to reduction in ovary volume, reduction in cyst size, complete dissolution of cyst and increased chances of pregnancy in infertile females.

A last object of the present invention is to disclose a method of treatment of PCOS comprising administering the said extract at a dosage of 1 gram per day in form of capsules of 500 mg twice a day, for a period of time ranging from 30-90 days, depending upon individual response and clinical assessment.

SUMMARY OF THE INVENTION

The invention discloses a single herb extract for the effective treatment of PCOS (Poly Cystic Ovarian Syndrome) when given in oral dosage form as capsules of 500 mg, twice a day for period of time ranging from 30-90 days. The extract is obtained from the seeds of fenugreek using a specific method of extraction and comprises five furostanolic saponins present in synergistic ratios as in Table 1 (Page 7) and having analytical profile as in FIG. 1.

DESCRIPTION OF THE ACCOMPANYING DRAWING

FIG. 1: Analytical fingerprint (LCMS profile) of extract of five furostanolic saponins from fenugreek seeds.

DETAILED DESCRIPTION OF THE INVENTION

The present invention discloses a furostanolic saponins extract comprising a synergistic mixture of five compounds, obtained from fenugreek seeds and suitable for the treatment of PCOS when given orally. The composition of the extract is given in Table 1 above and the analytical profile is disclosed in FIG. 1.

Dosage

Dosage forms of the above formulation were prepared in form of 500 mg capsules of the powder. Same were evaluated for clinical efficacy in the treatment of PCOS, after due approval of the ethical committee. Dosage given was 2 capsules per day, morning and evening after meals. Duration of administration of the extract varied between 30 days to 90 days (3 months). Number of subjects participating in the study was 50 and age group was 18-45 years. Results of the treatment are given below:

TABLE 2

Overall patient response using oral dosage form of present invention

| Parameter | No. of Patients | % | % of patients responded to treatment |
|---|---|---|---|
| Pregnant Patients | 6 | 12 | 94% |
| Patients with Complete dissolution of Cyst | 18 | 36 | (12 + 36 + 46) |
| Reduced cyst size | 23 | 46 | |
| No Response | 3 | 6 | |
| Total Patients | 50 | 100 | |

TABLE 3

Effect of oral dosage form of present invention on menstrual cycle

| Menstrual Cycle | Visits | | | | |
|---|---|---|---|---|---|
| | Baseline | 1 visit | 2visit | $3^{rd}$ visit | Total |
| Irregular Cycles | 2 | 2 | 1 | 0 | 5 |
| | 9.52% | 9.52% | 4.76% | 0.00% | 5.95% |
| Primary | 2 | 2 | 2 | 2 | 8 |

TABLE 3-continued

Effect of oral dosage form of present invention on menstrual cycle

| Menstrual Cycle | Visits | | | | |
|---|---|---|---|---|---|
| | Baseline | 1 visit | 2visit | 3$^{rd}$ visit | Total |
| infertilities | 9.52% | 9.52% | 9.52% | 9.52% | 9.52% |
| Prolonged Cycles | 17 | 17 | 11 | 4 | 49 |
| | 80.95% | 80.95% | 52.38% | 19.05% | 58.33% |
| Regular Cycles | 0 | 0 | 7 | 15 | 22 |
| | 0.00% | 0.00% | 33.33% | 71.43% | 26.19% |
| Total | 21 | 21 | 21 | 21 | 84 |
| | 100.0% | 100.0% | 100.0% | 100.0% | 100.0% |

At the time of enrollment most of the patients had prolonged menstrual cycle (81%) and irregular cycle (10%/). A few patients (10%/) had primary infertilities.

There was significant improvement in menstrual cycle with consumption of the fenugreek seed extract. On completion of the last visit 71% of patient had regular cycles, 19% patient reported prolonged cycle and approximately 10% reported primary infertility.

Results of the Study are Summarized Below:
a. Fenugreek seed extract of present invention caused significant reduction in ovary volume in patients of PCOS.
b. 46% of study population showed reduction in cyst size
c. 36% % of study population showed complete dissolution of cyst
d. 12% of patients got pregnant
e. 71% of patients reported regular menstrual cycle on completion of the treatment
f. Overall 94% of patients responded positively or got benefitted from the fenugreek extract dosing.

Safety Profile

Safety profile of the extract was evaluated. No significant changes were observed in serum liver function tests, serum renal function tests and hemograms in the patients. It was concluded based on the clinical results that administration of analytically defined extract of present invention, at a dosage of 500 mg twice a day for periods varying between 30-90 days, provided effective results in the treatment of PCOS.

Method of Use of the Invention

The extract is made into dosage forms of capsules of 500 mg each. When administered orally twice a day for periods varying between 30-90 days, the extract provided effective results in the treatment of PCOS.

Novelty—The invention discloses a novel herbal extract derived from a single herb and its method of use for the treatment of PCOS which has not been disclosed in the prior art. The extract comprises a synergistic mixture of five furostanolic saponins extracted from seeds of a single herb viz. fenugreek (Table 1 at Page 7 and FIG. 1). The extract when given orally at a dose of I gram per day (500 mg capsules, twice a day) for a period of time ranging from 30-90 days is effective in the treatment of PCOS.

Inventive step—The inventive steps lies in the technical advancement of knowledge for treatment of PCOS using extract obtained from a single herb and disclosure of its method of use (dosage per day for a fixed period of time i.e. 1 gram per day in form of 500 mg capsules, taken twice a day for period ranging from 30-90 days, as per clinical advise and assessment based on patient response). The novel extract is isolated from seeds of a single herb viz. fenugreek and comprises a synergistic mixture of five furostanolic saponins (Table 1 at Page 7 and FIG. 1) which are effective in the treatment of PCOS when given in appropriate dosage.

Industrial application—The said extract is suitable for the treatment of PCOS and can be manufactured on industrial scale.

Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention and best mode of performing the invention. It is therefore contemplated that such modifications can be made without departing from the spirit or scope of the present invention as defined and will be regarded within the scope of the present invention.

We claim:

1. A method for treating polycystic ovarian syndrome (PCOS) in a patient in need thereof comprising administering to the patient an effective amount of a composition consisting essentially of a single herbal extract obtained from fenugreek seeds as an active ingredient, said extract comprising a mixture of five furostanolic saponins comprising a first furostanolic saponin, a second furostanolic saponin, trigoneoside IV, glycoside F and protodioscin.

2. The method according to claim 1, wherein the effective amount is a dosage of one gram per day of the composition for a period of time ranging from 30 to 90 days.

3. The method according to claim 1, wherein the effective amount is a dosage of one gram per day of the composition administered twice a day in a capsule comprising 500 mg of the composition.

4. A method for treating polycystic ovarian syndrome (PCOS) in a patient in need thereof comprising administering to the patient an effective amount of a composition consisting essentially of a single herbal extract obtained from fenugreek seeds as an active ingredient, said extract comprising 7.13 weight % of a first furostanolic saponin, 4.61 weight % of a second furostanolic saponin, 15.10 weight % of trigoneoside IV, 29.36 weight % of glycoside F and 43.80 weight % of protodioscin.

5. The method according to claim 4, wherein the effective amount is a dosage of one gram per day of the composition for a period of time ranging from 30 to 90 days.

6. The method according to claim 4, wherein the effective amount is a dosage of one gram per day of the composition administered twice a day in a capsule comprising 500 mg of the composition.

* * * * *